United States Patent [19]

Abrams

[11] Patent Number: 5,334,165
[45] Date of Patent: Aug. 2, 1994

[54] FLUSH DEVICE

[76] Inventor: Lawrence M. Abrams, P.O. Box 5779, Englewood, N.J. 07631

[21] Appl. No.: 3,551

[22] Filed: Jan. 13, 1993

[51] Int. Cl.$^5$ .............................................. A61M 5/00
[52] U.S. Cl. ................................. 604/249; 137/599.1
[58] Field of Search ............... 604/118, 246, 248, 249; 137/599.1; 251/117; 128/673, 675, 748

[56] References Cited

U.S. PATENT DOCUMENTS

| | | | |
|---|---|---|---|
| 1,983,227 | 12/1934 | Hall et al. | 137/599.1 |
| 2,688,957 | 9/1954 | Culp | 137/599.1 |
| 4,457,487 | 7/1984 | Steigerwald | 604/249 |
| 4,624,662 | 11/1986 | Le | 604/249 |
| 4,822,344 | 4/1989 | O'Boyle | 604/248 |

Primary Examiner—John D. Yasko
Assistant Examiner—Anthony Gutowski
Attorney, Agent, or Firm—Herbert M. Shapiro

[57] ABSTRACT

A flush device comprising an inlet and an outlet chamber separated by a wall also includes two apertures in the wall. One of the apertures has a small diameter, the other having a large diameter. A serpentine-shaped capillary tube is formed along the wall surface in the inlet chamber and coaxial with the axis of the larger diameter aperture. The exit end of the tube is connected to the smaller diameter aperture for providing a controlled fluid path from the inlet to the outlet chamber. A plunger is positioned coaxially with the axis of the larger diameter aperture and is biased to normally close the larger diameter aperture. The plunger also is operative to open the larger diameter aperture for forming a large diameter path for fluids for a flush operation.

13 Claims, 6 Drawing Sheets

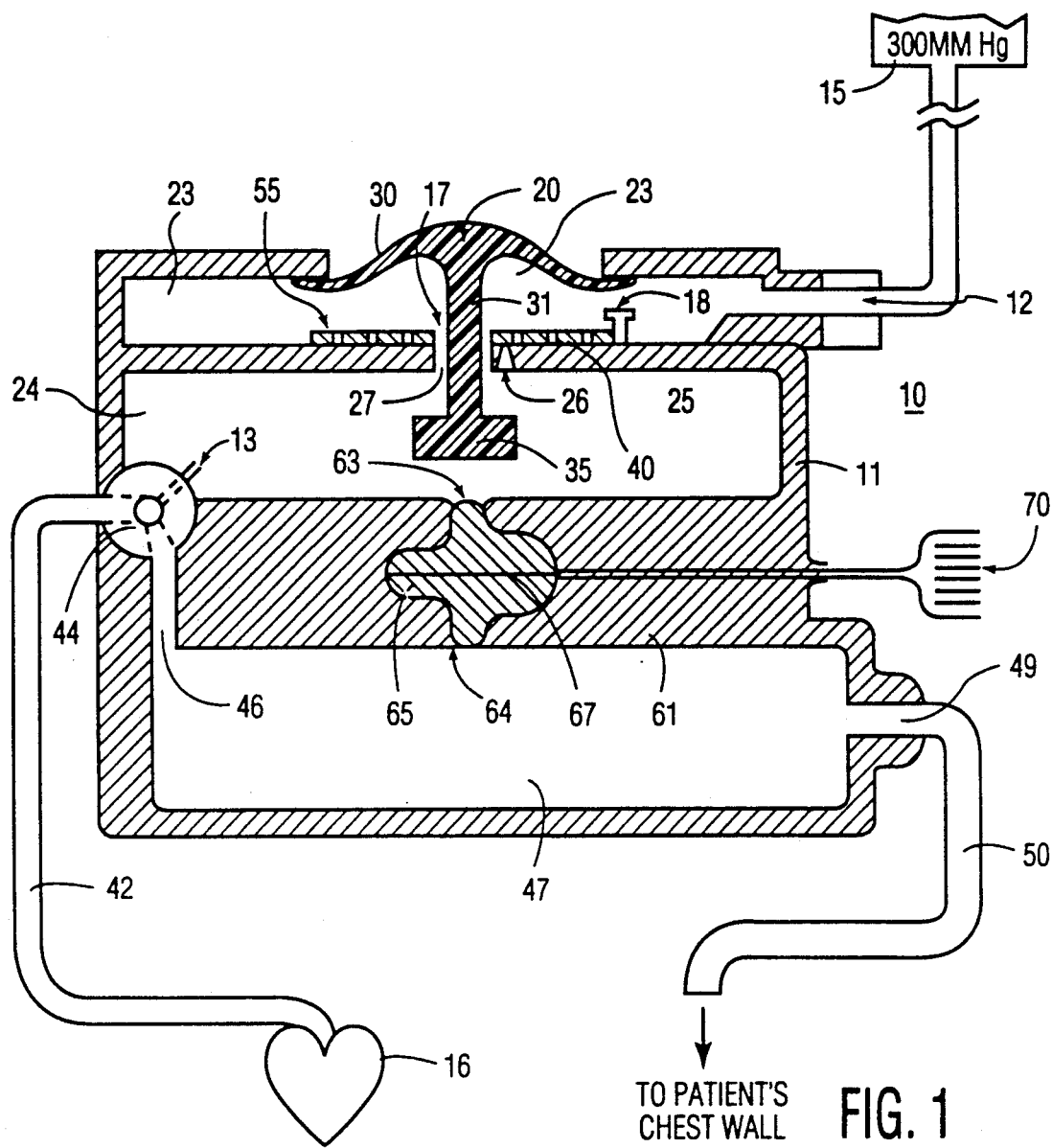
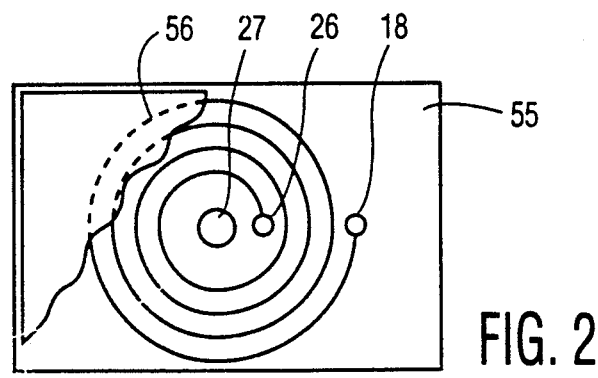
FIG. 1
FIG. 2

FLUSH DEVICE

FIELD OF THE INVENTION

This invention relates to a flush device which is a familiar component of a hospital fluid administration system to a patient.

BACKGROUND OF THE INVENTION

Frequently, a hospital stay involves the administration of controlled low flow fluids to a patient. This may be particularly so for acutely ill patients, such as those who have just had major surgery.

Flush devices are often employed to deliver controlled low fluid flow rates to patients. Flush devices are required to have certain characteristics. The first characteristic is that the flow be rated specific to the flush device and that it be accurate. The flow rate will often be a low or very low rate such as three cubic centimeters per hour. Second, the device must operate in this slow flush mode as it's default. Third, it must be able to be flushed at a much faster rate. The rapid flush should be possible only with operator input.

Currently available devices are often inaccurate due to very small dimension capillaries. Further, these capillaries are difficult to manufacture and expensive. They may leak and potentially lead to infection. Lastly, while all available flush devices allow switching between the default slow flush and the manual fast flush, none allow the device to be locked in the default slow flush mode. Cosequently, they may be inadvertantly fast flushed, causing dangerous quantities of fluid and/or air to enter the patient.

BRIEF DESCRIPTION OF THE INVENTION

A flush device in accordance with the principles of this invention includes a plunger which when moved from it's default closed position adds to the fluid flow normally moving in a capillary tube. The plunger opens a parallel relatively large diameter fluid path. The fluid path connects a source of fluid to the patient. The capillary tube is defined by a long, relatively wide bore conduit, rather than by the short, relatively narrow bore conduit of prior art devices. The capillary tube is positioned in parallel with, or within, the wider bore rapid flush tube and remains open during the flush operation.

BRIEF DESCRIPTION OF THE DRAWING

FIG. 1 is a schematic representation of a flush device in accordance with the principles of this invention in a fluid delivery system; FIGS. 2 and 3 are schematic representations of the capillary and control portions of a flush device of the type shown in FIG. 1;

DETAILED DESCRIPTION OF AN ILLUSTRATIVE EMBODIMENT OF THIS INVENTION

Figure 3:
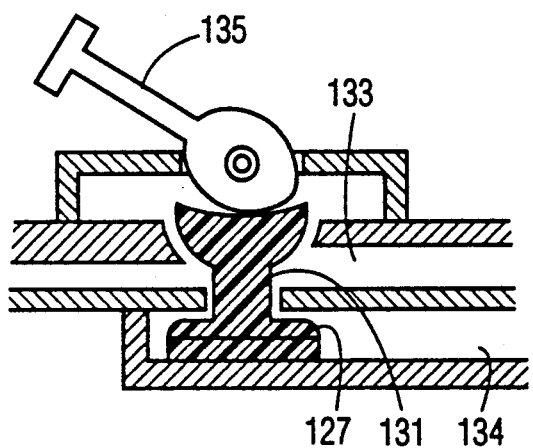

FIG. 1 shows a flush device integrated into a patient delivery system. The flush device is indicated by the numeral 10. The device comprises a housing 11 with inlet and outlet ports 12 and 13. In conventional rise, the inlet port is connected to a source 15 of fluid under pressure and the output port is connected to a patient's cardiovascular system indicated at 16. The housing of the device includes two fluid paths 17 and 18. Path 18 comprises a unique capillary tube and always remains open. The capillary tube is discussed in detail in connection with FIG. 2.

Path 17 is a relatively large diameter path and is used to flush out the system. Path 17 is used intermittently under the control of a health care specialist. The open or closed status of path 17 is controlled by a plunger 20 in one embodiment of this invention. Specifically, housing 11 is separated into two chambers 23 and 24 by a wall 25. Wall 25 has two openings in it. One opening 26 is connected to the capillary tube; the other, 27 is open or closed depending on the position of plunger 20.

The plunger, illustratively, is flexibly attached to the housing by plunger cap 30. The stem 31 of the plunger resides in opening 27 and moves along a vertical axis coincident with the axis of opening 27. Also, the plunger has an enlarged base area 35 larger than the diameter of opening 27. The main part of the stem has a diameter smaller than that of opening 27 so that when the plunger is in an elevated position, the base closes opening 27, and when the plunger is depressed, opening 27 is open for flushing out the system. The form of the plunger is only illustrative and the plunger may have a number of different shapes, all suitable for opening and closing opening 27. It is clear then that opening 27 permits a flush operation to occur when the plunger is moved to the "open" position.

The capillary tube is a small diameter tube starting in chamber 23 and passing through wall 25 at opening 26. The tube is always open permitting passage of a measured amount of fluid to a patient through outlet port 13, along tube 42 to cardiovascular system 16 via stopcock 44. But during a flush operation, the plunger is depressed and fluid flows into chamber 24 thus achieving the fast flush mode.

When the flush device is combined with a pressure compensating device as shown in FIG. 1, the device may also serve to purge air from the leveling fluid path. As shown in FIG. 1, when stopcock 44 is turned so that the fluid path 46 is closed off and fluid path 42 is opened, the flush device operates in the simple mode without pressure compensation. When the stopcock is turned so that fluid path 42 is closed and fluid path 46 is opened, the flushing operation purges air from chamber 47 and the tube/path 49/50. The fluid exiting tube 50 does not enter the patient, but is collected in the receptacle shown in the patient noted below. When the stopcock is kept in this second position (path 42 closed), during slow flush (default plunger closed) zeroing of the transducer is possible because the pressures are equal in chambers 24 and 47.

Chamber 47 communicates with a patient's chest wall via port 49 and tube 50 for providing a means for normalizing any unwanted changes in pressure due to changes in the vertical heights of various components of the system relative to one another as disclosed in U.S.

Pat. Ser. No. 5,098,384 issued Mar. 24, 1992 to the inventor of the present invention.

The capillary tube is of unique construction shown in FIG. 2. The tube has an inside diameter relatively large (3 millimeters or larger) when compared to prior art capillary tubes, the length compensating for the relatively large diameter. This unconventional approach to capillary tubes in a flush device permits an unconventional design of the device to be implemented.

FIG. 2 shows a top view of the capillary tube extending from chamber 23 of FIG. 1 (from 18), along the top of wall 25 to opening 26. The tube appears as a coil around opening 27 and may be defined, in one embodiment, as a depression in the top surface of wall 25 or in a ceramic slab 55. The depression in the slab may be formed by photoetching techniques or by silk screen techniques. The coil is covered by a flat cover of, for example, glass with an ultra violet sensitive adhesive which does not extend into the depression when set. The cover is shown, partially cut away, and is designated 56 in FIG. 2. If the depression (coil) is formed directly in wall 25, it is formed by molding techniques with a pressure sealed cap.

The housing includes a relatively thick wall has openings 63 and 64 and a pressure sensor 65 is placed in the wall so that it extends into both openings 63 and 64 as shown. Sensor 65 includes a diaphragm 67 which moves upwards or downwards, as viewed responsive to pressure changes in chambers 24 and 47. The sensor is connected electrically to a display indicated at 70. The sensor can be seen to be a "wet-wet" sensor of the type used in the system disclosed in the above-identified patent.

The flush device of FIG. 1 can thus be seen to comprise the portion of the figure above wall 61, as viewed, but is disclosed in the context of a gravity-compensated flow meter implementation of the invention disclosed in the above-identified patent.

The plunger configuration and operation of the plunger of FIG. 1 are merely illustrative. FIG. 3 shows a lever type plunger also suitable for operation of the device of FIG. 1. The figure shows a plunger stem 131 which has a distorted horizontal H shape configuration. The top of the stem is compressed into opening 127 to close off the relatively large aperture between chambers 133 and 134 when the lever arm 135 is in an upright position. The large aperture is open when the lever arm is not in an upright position as shown in the figure.

This alternativetype of arrangement also could be a substitute for the stopcock (44) of FIG. 1. When the lever forces down the rubber material, it also closes the fluid exit path 42 in FIG. 1. Since the lever can be positioned into the upright or the slant position and left in either position, it is operative as a switch that is either-/or but not continuous. A stop cock has the disadvantage of being partially open to both paths when the lever is only half turned, or it may be open to neither path, depending on the construction of the stopcock.

Figure 4:
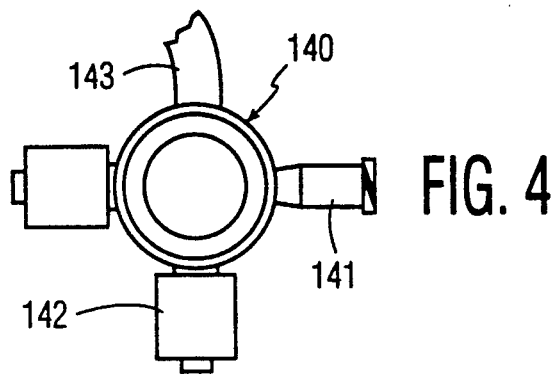
FIG. 4 is a top view of a practical flush device in accordance with the principles of this invention.
Figure 5:
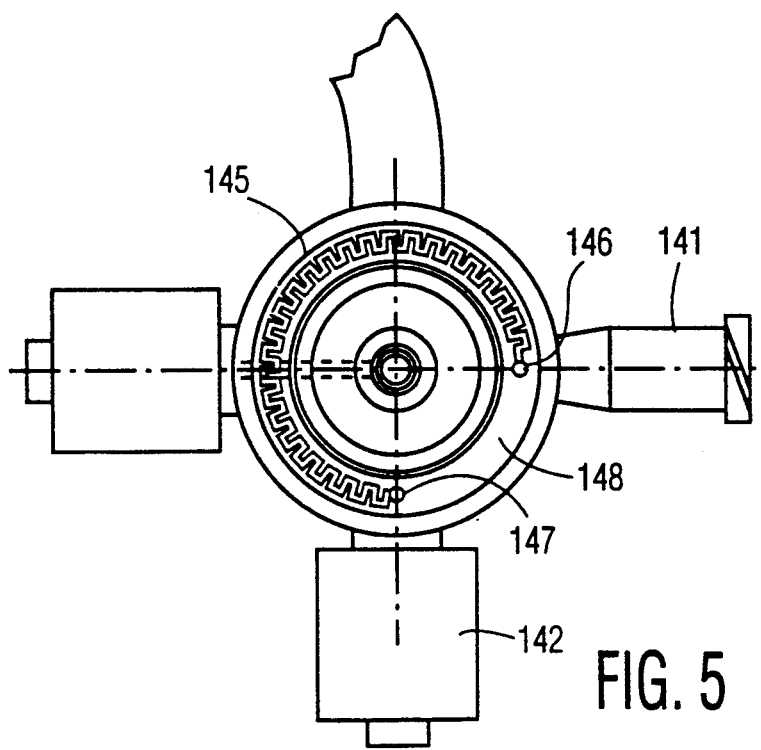
FIG. 5 is a top view of a potion of the device of FIG. 4.

FIG. 4 shows a schematic top view, full size, of a flush device 140 in accordance with the principles of this invention. The device includes input and output ports 141 and 142, respectively, and an interface cable 143 for embodiments including a pressure transducer. FIG. 5 shows a schematic enlarged view of the device of FIG. 4 showing a square wave shaped labyrinth of the capillary tube 145 of the device. The capillary tube extends between an input 141 (opening 146) and aperture 147 through wall 148, opening 146 and aperture 147 corresponding to inlet 18 and aperture 26 of FIG. 1.

Figure 6:
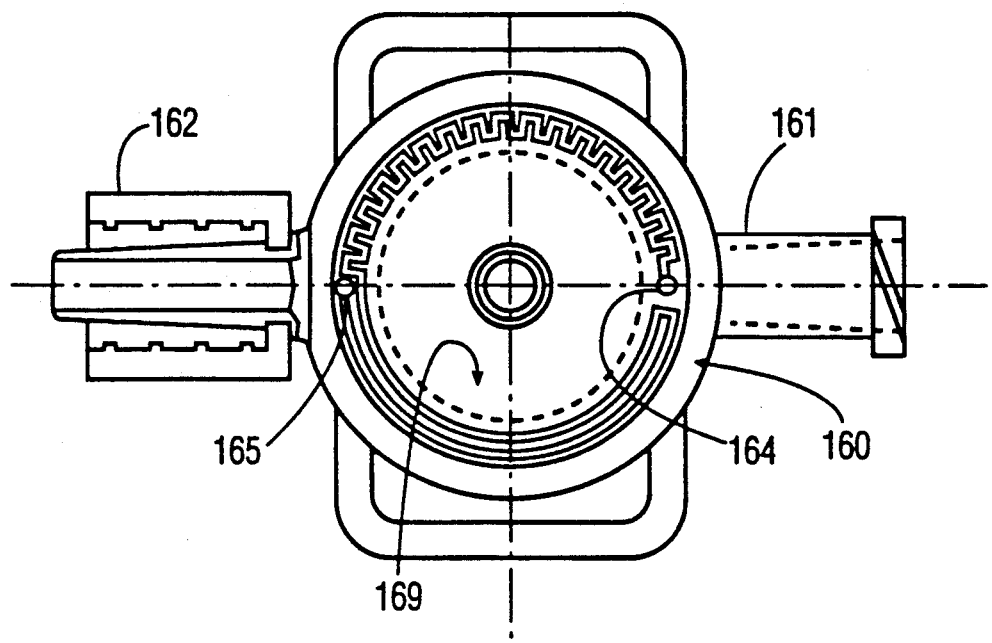
FIGS. 6 and 7 are top and cross sectional views of an alternative embodiment to the device of FIG. 4.

FIG. 6 shows an enlarged view of an alternative prototype flush device 160 in accordance with the principles of this invention. The device has inlet and outlet ports 161 and 162 respectively. The capillary tube, in this instance, is defined by a square wave shaped groove (as view from the top) which extends from an inlet opening 164 to outlet opening 165 through wall 169. The capillary, in this embodiment, can he seen to be square wave in shape only over one half the circumference of the device, extending in arcs back and forth over the other half circumference as shown.

Figure 7:
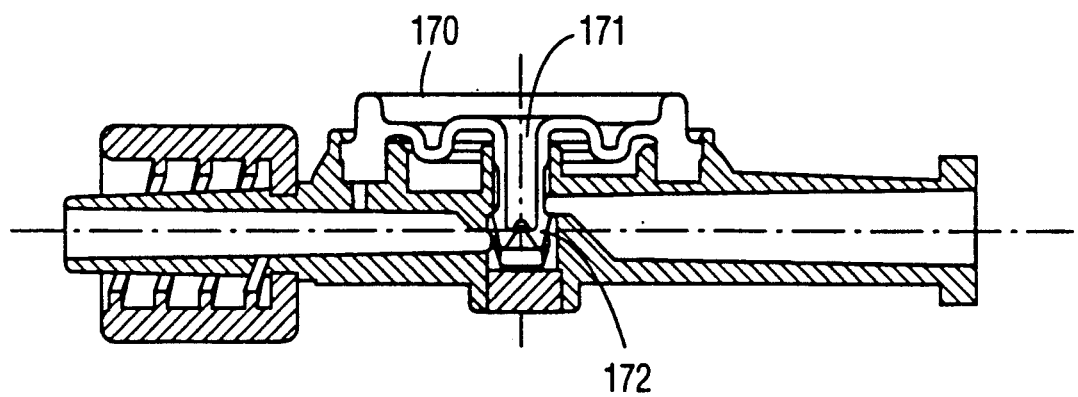

FIG. 7 shows a schematic cross sectional view of the device of FIG. 6. Most prominant in the view of FIG. 7 is the button 170 and the stem 171 of the button which controls the flush and the capillary mode of operation of the device. The stem has an enlarged base portion 172 with a relatively large diameter and a relatively small diameter stem portion. The opening in wall 169 through which the stem extends is larger than the stem diameter and smaller than the diameter of the base portion in order to pass fluid depending on whether the button is being depressed by an operator or is in the elevated position respectively.

Figure 8:
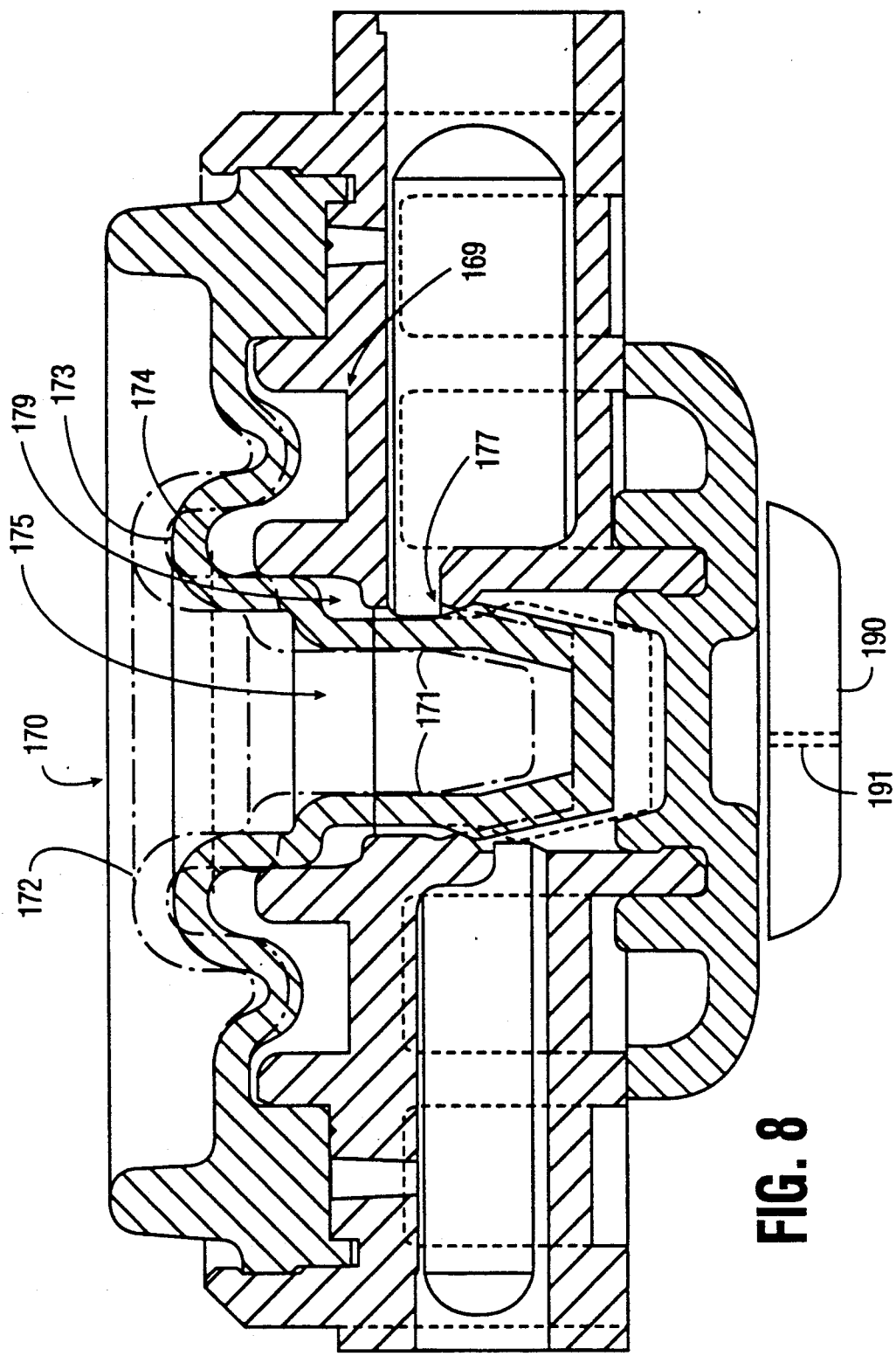
FIG. 8 is an enlarged schematic view of the device of FIG. 5.

FIG. 8 shows an enlarged cross section of the flush device of FIG. 7. The figure shows the button in several different positions. The top position, represented by broken curved line 172, indicates the original position of the button when the device is molded. Curved lines 173 and 174 represent the positions of the button during the rest and the flush modes of operation respectively. The opening 175 in wall 169 through which stem 171 extends can be seen to fit loosely about the stem at 177 but engages the base portion of the stem when that portion is elevated.

When the stem is elevated, a chamber 179 is formed which fills with fluid. The fluid in chamber 179 creates a pressure which aids in retaining the button in the elevated position.

Figure 9:
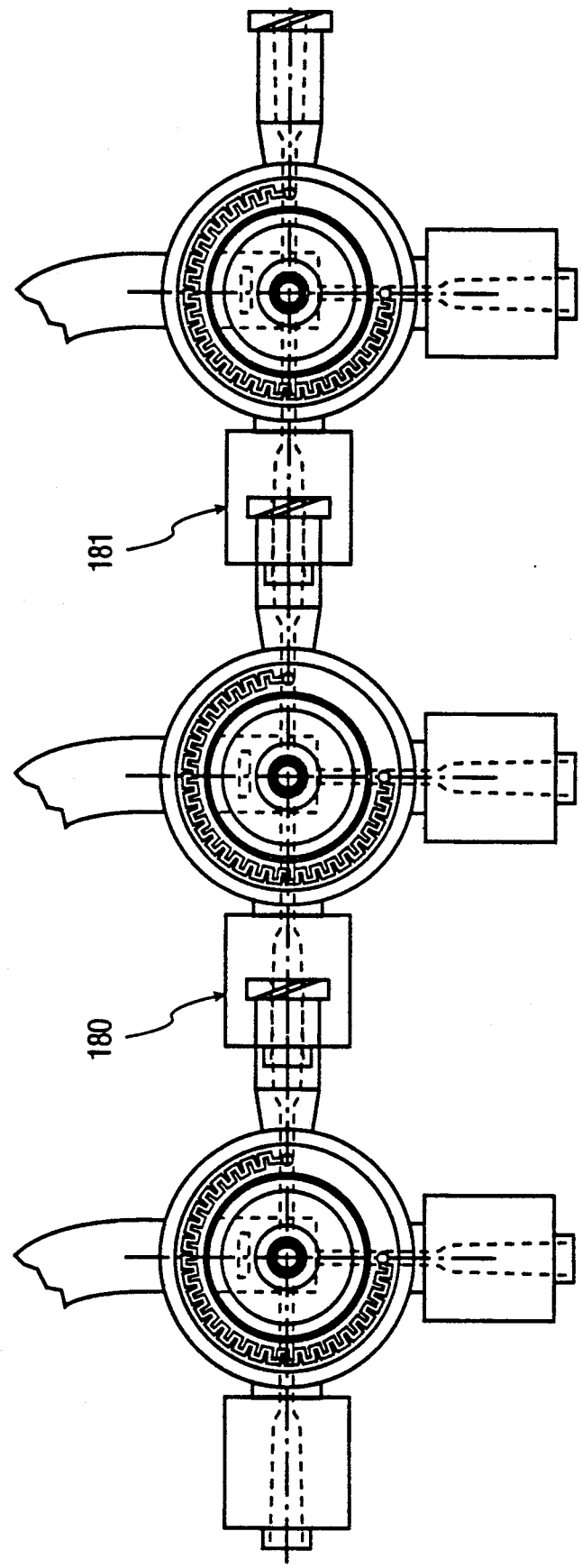
FIGS. 9 and 10 schematic top and cross section views of stacked devices of the type shown in FIG. 5.
Figure 10:
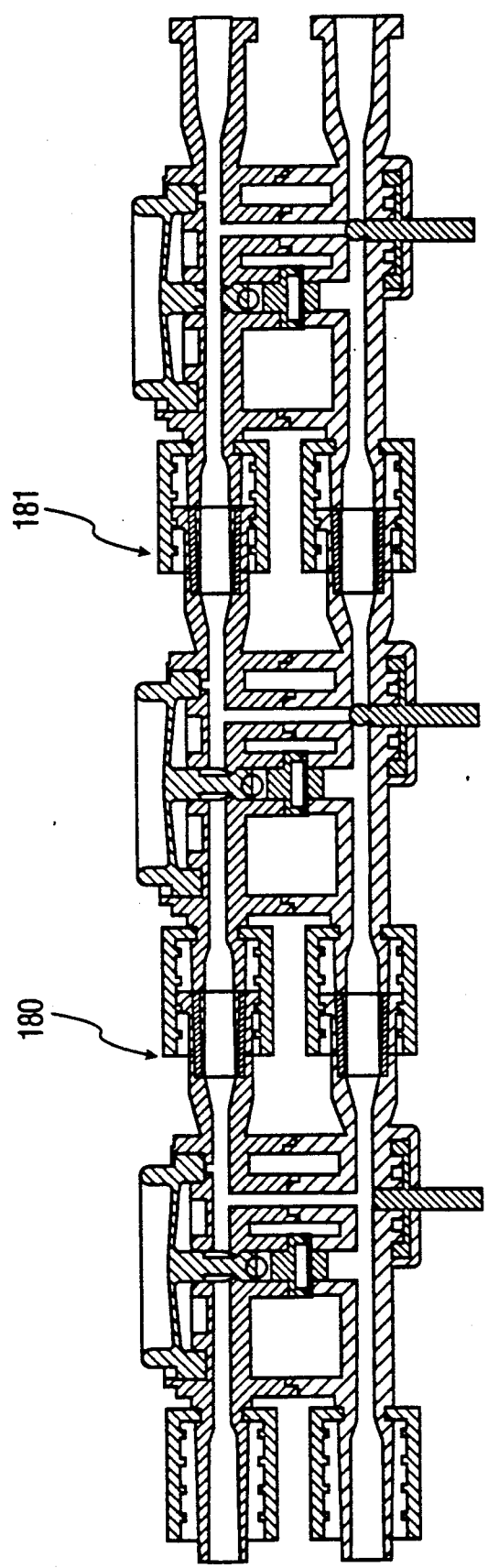

FIGS. 9 and 10 show a top and a schematic cross section view, respectively, of stackable flush devices with transducers and adapted for pressure compensation as described in the above identified patent. The figures show a plurality of such devices stacked as is frequently the case when in use in hospitals. The devices are mated, inlet to outlet port, at 180 and 181 as shown. The entire actual length of the plurality of devices as shown (full size) is 5.280 inches.

FIGS. 5, 6, 7, and 8 also show dimensions for a molded three piece assembly for a flush device in which the housing is made of polycarbonate and the button is polyethylene. The capillary tube is seen to have a V-shaped geometry and is 3.6 inches long as shown in FIG. 5. The inlet and outlet diameters for the device are .170 and .156 inches, respectfully, as shown in FIG. 6 and the capillary dimensions are .008 inches wide×.005 inches deep defining an angle of ninety degrees. The outside diameter of the housing is .900 inches and the button has a diameter of .580 inches. Various other dimensions are shown in the enlarged FIG. 8.

FIG. 8 also shows a locking arrangement to prevent the movement of the plunger. The locking arrangement comprises a button 190 at the bottom of FIG. 8, as viewed. The button includes an interior wall 191. The button is rotatable about a center axis and thus is operative to move the wall between first and second positions. The plunger stem, in this instance, includes an extension (not shown) to engage that wall, or not, depending on the position of the wall.

What is claimed is:

1. A flush device comprising a housing and including first and second paths for fluid passage therein, said device including a first wall separating said housing into entrance and exit chambers, said wall having first and second apertures therethrough, said entrance chamber including an entrance port for introducing fluid into said entrance chamber, said exit chamber including an exit port for fluids exiting said exit cheer, said entrance chamber including a capillary tube connected to said first aperture and open to said first and second chambers, control means movable between first and second positions for opening and closing said second aperture to fluid passage respectively for obtaining a fast flush mode only under attendant control, said capillary having an elongated geometry along an arcuate path on the surface of said wall, said device including a fluid path connected to said exit port and adapted for insertion into a patient.

2. A flush device as set forth in claim 1 also including first means for defining a third chamber, second means for controllably connecting said exit and said third chamber, and transducer means connected between said exit and third chamber, said third chamber being connected to air, said exit chamber being adapted for connection to a patient, said first means being operative to interrupt fluid flow to said patient or to said third chamber when set to first or second positions respectively.

3. A flush device as set forth in claim 1 wherein said capillary tube is defined by a square wave geometry arranged along a curvilinear path about said second aperture, said curvilinear path being open at an input end to said entrance chamber and being connected to said first aperture at an exit end thereof.

4. A flush device as set forth in claim 3 wherein said capillary tube has a spiral geometry coaxial with the axis of said second aperture.

5. A flush device as set forth in claim 1 wherein said capillary tube is formed as a recess in the surface of a rigid block of material and completed by a planar capping member secured to said surface.

6. A flush device as set forth in claim 4 wherein said capillary tube is formed as a recess in the surface of a rigid block of material and completed by a planar capping member secured to said surface.

7. A flush device as set forth in claim 1 wherein said said control means comprises a plunger, said plunger including a flexible head portion relatively large in diameter and a stem portion of relatively small diameter compared to the diameter of said second aperture, said plunger also having a base portion having a diameter large compared to that of said second aperture, said base portion being operative to seal said second aperture when said plunger is in an elevated position.

8. A flush device as set forth in claim 1 further including a third chamber, wherein said exit chamber includes said exit port and a stop cock means for diverting fluid flow from said exit port to said third chamber, said third chamber including a second exit port, said device including a pressure sensor having first and second surfaces communicating with said exit and third chambers respectively.

9. A flush device as set forth in claim 1 also including a locking arrangement to selectively prevent said control means from being moved to said first position.

10. A flush device as set forth in claim 1 wherein said capillary is formed in the surface of said wall.

11. A flush device as set forth in claim 2 wherein said capillary tube is defined by a square wave geometry arranged along a curvilinear path about said second aperture, said curvilinear path being open at an input end to said entrance chamber and being connected to said first aperture at an exit end thereof.

12. A flush device as set forth in claim 11 wherein said capillary tube has a spiral geometry coaxial with the axis of said second aperture.

13. A flush device as set forth in claim 2 wherein said capillary tube is formed as a recess in the surface of a rigid block of material and completed by a planar capping member secured to said surface.

* * * * *